United States Patent
Eversull et al.

(10) Patent No.: US 11,633,213 B2
(45) Date of Patent: *Apr. 25, 2023

(54) CATHETER SYSTEMS WITH IMAGING ASSEMBLIES

(71) Applicant: Intuitive Surgical Operations, Inc., Sunnyvale, CA (US)

(72) Inventors: Christian S. Eversull, Palo Alto, CA (US); Stephen A. Leeflang, Sunnyvale, CA (US); Nicholas J. Mourlas, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/406,819

(22) Filed: Aug. 19, 2021

(65) Prior Publication Data
US 2021/0378706 A1 Dec. 9, 2021

Related U.S. Application Data

(60) Continuation of application No. 17/345,768, filed on Jun. 11, 2021, which is a continuation of application
(Continued)

(51) Int. Cl.
*A61B 1/00* (2006.01)
*A61B 1/005* (2006.01)
(Continued)

(52) U.S. Cl.
CPC ........ *A61B 17/3468* (2013.01); *A61B 1/0051* (2013.01); *A61B 1/0057* (2013.01);
(Continued)

(58) Field of Classification Search
CPC ..... A61B 1/00082; A61B 1/05; A61B 1/3137; A61B 17/3468; A61B 17/00234
See application file for complete search history.

(56) References Cited

U.S. PATENT DOCUMENTS

| 1,060,665 A | 5/1913 | Charles |
| 2,574,840 A | 11/1951 | Pieri et al. |

(Continued)

FOREIGN PATENT DOCUMENTS

| CN | 103097086 A | 5/2013 |
| EP | 0283661 A2 | 9/1988 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
(Continued)

*Primary Examiner* — Matthew J Kasztejna
(74) *Attorney, Agent, or Firm* — Haynes and Boone, LLP

(57) ABSTRACT

A catheter system comprises an elongate catheter body including a distal end, a cannulation lumen extending through the catheter body and terminating at the distal end of the catheter body, and a steering element extending through the catheter body for steering the distal end. The catheter system also comprises an imaging element secured to a distal end portion of the catheter body and configured to obtain optical images of an area located distally of the distal end of the catheter body. The catheter body includes a ridge extending axially along an outer surface of the distal end portion, wherein a width of the ridge measured about a circumference of the catheter body is less than a length of the ridge measured along the longitudinal axis, and the imaging element is radially aligned with the ridge with at
(Continued)

least a portion of the imaging element disposed within the ridge.

19 Claims, 8 Drawing Sheets

Related U.S. Application Data

No. 16/459,504, filed on Jul. 1, 2019, now Pat. No. 11,058,458, which is a continuation of application No. 15/175,601, filed on Jun. 7, 2016, now Pat. No. 10,368,910, which is a continuation of application No. 14/591,278, filed on Jan. 7, 2015, now abandoned, which is a division of application No. 11/465,123, filed on Aug. 16, 2006, now Pat. No. 8,956,280, which is a continuation-in-part of application No. 11/379,562, filed on Apr. 20, 2006, now abandoned, which is a continuation-in-part of application No. 11/269,976, filed on Nov. 8, 2005, now Pat. No. 8,016,748, said application No. 11/269,976 is a division of application No. 10/447,526, filed on May 29, 2003, now Pat. No. 6,979,290.

(60) Provisional application No. 60/708,747, filed on Aug. 16, 2005, provisional application No. 60/384,262, filed on May 30, 2002.

(51) Int. Cl.
| | |
|---|---|
| *A61B 1/018* | (2006.01) |
| *A61B 17/34* | (2006.01) |
| *A61B 1/313* | (2006.01) |
| *A61N 1/05* | (2006.01) |
| *A61B 1/015* | (2006.01) |
| *A61B 1/05* | (2006.01) |
| *A61B 17/00* | (2006.01) |
| *A61M 25/09* | (2006.01) |
| *A61B 90/00* | (2016.01) |
| *A61M 25/01* | (2006.01) |

(52) U.S. Cl.
CPC ...... *A61B 1/00073* (2013.01); *A61B 1/00082* (2013.01); *A61B 1/00154* (2013.01); *A61B 1/015* (2013.01); *A61B 1/018* (2013.01); *A61B 1/05* (2013.01); *A61B 1/051* (2013.01); *A61B 1/053* (2013.01); *A61B 1/3137* (2013.01); *A61B 17/00234* (2013.01); *A61M 25/09* (2013.01); *A61N 1/056* (2013.01); *A61N 1/057* (2013.01); *A61N 1/059* (2013.01); *A61N 1/0587* (2013.01); *A61B 2017/00243* (2013.01); *A61B 2017/00296* (2013.01); *A61B 2017/3488* (2013.01); *A61B 2090/3614* (2016.02); *A61M 2025/0177* (2013.01)

(56) References Cited

U.S. PATENT DOCUMENTS

| | | |
|---|---|---|
| 2,688,329 A | 9/1954 | Wallace |
| 3,162,190 A | 12/1964 | Gizzo |
| 3,452,740 A | 7/1969 | Wolf |
| 3,690,769 A | 9/1972 | Toshiyuki |
| 3,866,599 A | 2/1975 | Johnson |
| 3,974,834 A | 8/1976 | Kane |
| 4,033,331 A | 7/1977 | Guss et al. |
| 4,224,929 A | 9/1980 | Furihata |
| 4,392,853 A | 7/1983 | Muto |
| 4,401,433 A | 8/1983 | Luther |
| 4,406,656 A | 9/1983 | Hattler et al. |
| 4,451,256 A | 5/1984 | Weikl et al. |
| 4,470,407 A | 9/1984 | Hussein |
| 4,569,347 A | 2/1986 | Frisbie |
| 4,581,017 A | 4/1986 | Sahota et al. |
| 4,601,713 A | 7/1986 | Fuqua |
| 4,619,247 A | 10/1986 | Inoue et al. |
| 4,650,472 A | 3/1987 | Bates |
| 4,689,041 A | 8/1987 | Corday et al. |
| 4,710,181 A | 12/1987 | Fuqua |
| 4,717,387 A | 1/1988 | Inoue et al. |
| 4,723,936 A | 2/1988 | Buchbinder et al. |
| 4,738,666 A | 4/1988 | Fuqua |
| 4,779,611 A | 10/1988 | Grooters et al. |
| 4,781,681 A | 11/1988 | Sharrow et al. |
| 4,784,133 A | 11/1988 | Mackin |
| 4,800,876 A | 1/1989 | Fox et al. |
| 4,886,067 A | 12/1989 | Palermo |
| 4,898,577 A | 2/1990 | Badger et al. |
| 4,921,479 A | 5/1990 | Grayzel |
| 4,960,411 A | 10/1990 | Buchbinder |
| 4,961,738 A | 10/1990 | Mackin |
| 4,976,710 A | 12/1990 | Mackin |
| 4,991,578 A | 2/1991 | Cohen |
| 4,995,878 A | 2/1991 | Rai |
| 5,015,239 A | 5/1991 | Browne |
| 5,029,574 A | 7/1991 | Shimamura et al. |
| 5,060,660 A | 10/1991 | Gambale et al. |
| 5,090,959 A | 2/1992 | Samson et al. |
| 5,114,414 A | 5/1992 | Buchbinder |
| 5,116,317 A | 5/1992 | Carson, Jr. et al. |
| 5,125,895 A | 6/1992 | Buchbinder et al. |
| 5,147,317 A | 9/1992 | Shank et al. |
| 5,188,596 A | 2/1993 | Condon et al. |
| 5,190,528 A | 3/1993 | Fonger et al. |
| 5,201,756 A | 4/1993 | Horzewski et al. |
| 5,203,772 A | 4/1993 | Hammerslag et al. |
| 5,234,425 A | 8/1993 | Fogarty et al. |
| 5,246,420 A | 9/1993 | Kraus et al. |
| 5,254,084 A | 10/1993 | Geary |
| 5,254,088 A | 10/1993 | Lundquist et al. |
| 5,256,150 A | 10/1993 | Quiachon et al. |
| 5,263,932 A | 11/1993 | Jang |
| 5,271,383 A | 12/1993 | Wilk |
| 5,273,535 A | 12/1993 | Edwards et al. |
| 5,275,151 A | 1/1994 | Shockey et al. |
| 5,304,134 A | 4/1994 | Kraus et al. |
| 5,318,525 A | 6/1994 | West et al. |
| 5,325,845 A | 7/1994 | Adair |
| 5,336,252 A | 8/1994 | Cohen |
| 5,345,937 A | 9/1994 | Middleman et al. |
| 5,346,504 A | 9/1994 | Ortiz et al. |
| 5,358,478 A | 10/1994 | Thompson et al. |
| 5,358,479 A | 10/1994 | Wilson |
| 5,360,403 A | 11/1994 | Mische et al. |
| 5,389,073 A | 2/1995 | Imran |
| 5,391,147 A | 2/1995 | Imran et al. |
| 5,395,349 A | 3/1995 | Quiachon et al. |
| 5,409,469 A | 4/1995 | Schaerf |
| 5,409,483 A | 4/1995 | Campbell et al. |
| 5,413,560 A | 5/1995 | Solar |
| 5,431,676 A | 7/1995 | Dubrul et al. |
| 5,447,497 A | 9/1995 | Sogard et al. |
| 5,464,395 A | 11/1995 | Faxon et al. |
| 5,472,418 A | 12/1995 | Palestrant |
| 5,489,270 A | 2/1996 | Van Erp |
| 5,498,239 A | 3/1996 | Galel et al. |
| 5,505,686 A | 4/1996 | Willis et al. |
| 5,573,517 A | 11/1996 | Bonutti et al. |
| 5,588,432 A | 12/1996 | Crowley |
| 5,593,405 A | 1/1997 | Osypka |
| 5,611,777 A | 3/1997 | Bowden et al. |
| 5,617,854 A | 4/1997 | Munsif |
| 5,618,267 A | 4/1997 | Palestrant |
| 5,643,175 A | 7/1997 | Adair |
| 5,674,240 A | 10/1997 | Bonutti et al. |
| 5,713,867 A | 2/1998 | Morris |
| 5,735,831 A | 4/1998 | Johnson et al. |
| 5,738,649 A | 4/1998 | Macoviak |
| 5,741,320 A | 4/1998 | Thornton et al. |
| 5,752,518 A | 5/1998 | McGee et al. |

(56) References Cited

U.S. PATENT DOCUMENTS

| | | | |
|---|---|---|---|
| 5,762,604 A | 6/1998 | Kieturakis |
| 5,810,776 A | 9/1998 | Bacich et al. |
| 5,824,005 A | 10/1998 | Motamedi et al. |
| 5,824,041 A | 10/1998 | Lenker et al. |
| 5,827,227 A | 10/1998 | Delago |
| 5,855,569 A | 1/1999 | Komi et al. |
| 5,857,760 A | 1/1999 | Pelton |
| 5,876,373 A | 3/1999 | Giba et al. |
| 5,876,426 A | 3/1999 | Kume et al. |
| 5,902,331 A | 5/1999 | Bonner et al. |
| 5,908,435 A | 6/1999 | Samuels |
| 5,911,702 A | 6/1999 | Romley et al. |
| 5,935,102 A | 8/1999 | Bowden et al. |
| 5,938,586 A | 8/1999 | Wilk et al. |
| 5,944,691 A | 8/1999 | Querns et al. |
| 5,961,499 A | 10/1999 | Bonutti et al. |
| 5,968,010 A | 10/1999 | Waxman et al. |
| 5,997,508 A | 12/1999 | Lunn et al. |
| 6,007,517 A | 12/1999 | Anderson |
| 6,028,622 A | 2/2000 | Suzuki |
| 6,035,224 A | 3/2000 | West |
| 6,036,685 A | 3/2000 | Mueller |
| 6,086,557 A | 7/2000 | Morejohn et al. |
| 6,090,072 A | 7/2000 | Kratoska et al. |
| 6,096,036 A | 8/2000 | Bowe et al. |
| 6,099,498 A | 8/2000 | Addis |
| 6,110,145 A | 8/2000 | Macoviak |
| 6,120,477 A | 9/2000 | Campbell et al. |
| 6,122,552 A | 9/2000 | Tockman et al. |
| 6,134,460 A | 10/2000 | Chance |
| 6,178,346 B1 | 1/2001 | Amundson et al. |
| 6,179,827 B1 | 1/2001 | Davis et al. |
| 6,183,443 B1 | 2/2001 | Kratoska et al. |
| 6,197,016 B1 | 3/2001 | Fourkas et al. |
| 6,210,407 B1 | 4/2001 | Webster |
| 6,277,064 B1 | 8/2001 | Yoon |
| 6,283,951 B1 | 9/2001 | Flaherty et al. |
| 6,312,406 B1 | 11/2001 | Jayaraman |
| 6,338,730 B1 | 1/2002 | Bonutti et al. |
| 6,361,528 B1 | 3/2002 | Wilson et al. |
| 6,423,055 B1 | 7/2002 | Farr et al. |
| 6,458,107 B1 | 10/2002 | Ockuly |
| 6,464,631 B1 | 10/2002 | Girke et al. |
| 6,542,781 B1 | 4/2003 | Koblish et al. |
| 6,562,049 B1 | 5/2003 | Norlander et al. |
| 6,579,278 B1 | 6/2003 | Bencini |
| 6,585,718 B2 | 7/2003 | Hayzelden et al. |
| 6,592,581 B2 | 7/2003 | Bowe |
| 6,610,007 B2 | 8/2003 | Belson et al. |
| 6,616,628 B2 | 9/2003 | Hayzelden |
| 6,626,900 B1 | 9/2003 | Sinofsky et al. |
| 6,638,268 B2 | 10/2003 | Niazi |
| 6,652,492 B1 | 11/2003 | Bell |
| 6,692,430 B2 | 2/2004 | Adler |
| 6,730,058 B2 | 5/2004 | Hayzelden |
| 6,743,196 B2 | 6/2004 | Barbut et al. |
| 6,743,227 B2 | 6/2004 | Seraj et al. |
| 6,755,812 B2 | 6/2004 | Peterson et al. |
| 6,783,510 B1 | 8/2004 | Gibson et al. |
| 6,796,939 B1 | 9/2004 | Hirata et al. |
| 6,800,056 B2 | 10/2004 | Tartaglia et al. |
| 6,814,715 B2 | 11/2004 | Bonutti et al. |
| 6,869,414 B2 | 3/2005 | Simpson et al. |
| 6,899,673 B2 | 5/2005 | Ogura et al. |
| 6,979,290 B2 | 12/2005 | Mourlas et al. |
| 6,984,232 B2 | 1/2006 | Vanney et al. |
| 7,186,214 B2 | 3/2007 | Ness |
| 7,191,015 B2 | 3/2007 | Lamson et al. |
| 7,309,328 B2 | 12/2007 | Kaplan et al. |
| 7,610,104 B2 | 10/2009 | Kaplan et al. |
| 7,875,049 B2 | 1/2011 | Eversull et al. |
| 8,956,280 B2 | 2/2015 | Eversull et al. |
| 10,368,910 B2 | 8/2019 | Eversull et al. |
| 11,058,458 B2 | 7/2021 | Eversull et al. |
| 2001/0007927 A1 | 7/2001 | Koblish et al. |
| 2001/0007937 A1 | 7/2001 | Mackin |
| 2001/0039418 A1 | 11/2001 | Schaer |
| 2001/0053919 A1 | 12/2001 | Kieturakis et al. |
| 2002/0065512 A1 | 5/2002 | Fjeld et al. |
| 2002/0095117 A1 | 7/2002 | Wilson et al. |
| 2002/0099431 A1 | 7/2002 | Armstrong et al. |
| 2002/0120252 A1 | 8/2002 | Brock et al. |
| 2002/0123765 A1 | 9/2002 | Sepetka et al. |
| 2002/0165598 A1 | 11/2002 | Wahr et al. |
| 2003/0065353 A1 | 4/2003 | Horzewski et al. |
| 2003/0088154 A1* | 5/2003 | Ishibiki ............. A61B 1/00089 600/127 |
| 2003/0092995 A1 | 5/2003 | Thompson |
| 2003/0176766 A1 | 9/2003 | Long et al. |
| 2003/0233115 A1 | 12/2003 | Eversull et al. |
| 2004/0006344 A1 | 1/2004 | Nguyen et al. |
| 2004/0009155 A1 | 1/2004 | Palasis et al. |
| 2004/0039371 A1 | 2/2004 | Tockman et al. |
| 2004/0054724 A1 | 3/2004 | Sudo |
| 2004/0059257 A1 | 3/2004 | Gaber |
| 2004/0073286 A1 | 4/2004 | Armstrong et al. |
| 2004/0082832 A1* | 4/2004 | Moriyama ......... A61B 1/00089 600/101 |
| 2004/0087968 A1 | 5/2004 | Core |
| 2004/0210278 A1 | 10/2004 | Boll et al. |
| 2004/0220470 A1 | 11/2004 | Karmarkar et al. |
| 2004/0267092 A1 | 12/2004 | Ishibiki |
| 2005/0027243 A1 | 2/2005 | Gibson et al. |
| 2005/0085842 A1 | 4/2005 | Eversull et al. |
| 2005/0149105 A1 | 7/2005 | Leeflang et al. |
| 2005/0197530 A1 | 9/2005 | Wallace et al. |
| 2005/0197623 A1 | 9/2005 | Leeflang et al. |
| 2005/0228452 A1 | 10/2005 | Mourlas et al. |
| 2007/0015964 A1 | 1/2007 | Eversull et al. |
| 2007/0016130 A1 | 1/2007 | Leeflang et al. |
| 2009/0299363 A1 | 12/2009 | Saadat et al. |
| 2011/0034790 A1 | 2/2011 | Mourlas et al. |
| 2015/0133926 A1 | 5/2015 | Bhatt et al. |
| 2015/0190172 A1 | 7/2015 | Eversull et al. |
| 2016/0051130 A1 | 2/2016 | Mitsuya |
| 2021/0298789 A1 | 9/2021 | Eversull et al. |

FOREIGN PATENT DOCUMENTS

| | | |
|---|---|---|
| EP | 0818214 A2 | 1/1998 |
| EP | 0842673 A1 | 5/1998 |
| RU | 2168927 C2 | 6/2001 |
| WO | WO-8401512 A1 | 4/1984 |
| WO | WO-9729680 A1 | 8/1997 |
| WO | WO-9740880 A1 | 11/1997 |
| WO | WO-9829026 A2 | 7/1998 |
| WO | WO-0024310 A1 | 5/2000 |
| WO | WO-0103766 A1 | 1/2001 |
| WO | WO-0149356 A1 | 7/2001 |
| WO | WO-0172368 A2 | 10/2001 |
| WO | WO-0230310 A1 | 4/2002 |
| WO | WO-03037416 A1 | 5/2003 |
| WO | WO-03039350 A2 | 5/2003 |
| WO | WO-03053491 A2 | 7/2003 |
| WO | WO-03073942 A2 | 9/2003 |
| WO | WO-03090834 A2 | 11/2003 |
| WO | WO-2011002593 A1 | 1/2011 |
| WO | WO-2015049095 A1 | 4/2015 |

OTHER PUBLICATIONS

Final Office Action dated Jul. 9, 2010 for U.S. Appl. No. 11/269,976, filed Nov. 8, 2005.
Final Office Action dated Nov. 9, 2010 for U.S. Appl. No. 11/269,976, filed Nov. 8, 2005.
Final Office Action dated Jul. 12, 2010 for U.S. Appl. No. 11/379,562, filed Apr. 20, 2006.
Final Office Action dated Aug. 25, 2005 for U.S. Appl. No. 10/447,526, filed May 29, 2003.
Fujimura O., et al., "Direct in Vivo Visualization of Right Cardiac Anatomy by Fiberoptic Endoscopy. Hemodynamic Effects and Image Validation," Angiology, 1995, vol. 46 (3), pp. 201-209.

(56) References Cited

OTHER PUBLICATIONS

Fujimura O., et al., "Direct in Vivo Visualization of Right Cardiac Anatomy by Fibreoptic Endoscopy: Observation of Radiofrequency-Induced Acute Lesions Around the Ostium of the Coronary Sinus," European Heart Journal, 1994, vol. 15 (4), pp. 534-540.

International Search Report and Written Opinion for Application No. PCT/US2005/005425, dated Aug. 3, 2005, 13 pages.

International Search Report and Written Opinion for Application No. PCT/US2006/017785, dated Sep. 19, 2006, 11 pages.

International Search Report and Written Opinion for Application No. PCT/US2007/075644, dated Jun. 10, 2008, 4 pages.

International Search Report for Application No. PCT/US2004/032374, dated May 13, 2005, 4 pages.

Kuo C.S., et al., "In Vivo Angioscopic Visualization of Right Heart Structure in Dogs by Means of a Balloon-Tipped Fiberoptic Endoscope: Potential Role in Percutaneous Ablative Procedures," American Heart Journal, 1994, vol. 127 (1), pp. 187-197.

Moser K.M., et al., "Angioscopic Visualization of Pulmonary Emboli," Chest, 1980, vol. 77 (2), pp. 198-201.

Non-Final Office Action dated May 10, 2005 for U.S. Appl. No. 10/447,526, filed May 29, 2003.

Non-Final Office Action dated Nov. 12, 2009 for U.S. Appl. No. 11/269,976, filed Nov. 8, 2005.

Non-Final Office Action dated Dec. 13, 2006 for U.S. Appl. No. 10/958,034, filed Oct. 4, 2004.

Non-Final Office Action dated Oct. 23, 2009 for U.S. Appl. No. 11/379,562, filed Apr. 20, 2006.

Non-Final Office Action dated Oct. 24, 2006 for U.S. Appl. No. 10/447,526, filed May 29, 2003.

Notice of Allowance dated Sep. 29, 2005 for U.S. Appl. No. 10/447,526, filed May 29, 2003.

Requirement for Restriction/Election dated Oct. 19, 2006 for U.S. Appl. No. 10/958,034, filed Oct. 4, 2004.

Requirement for Restriction/Election dated Jan. 31, 2005 for U.S. Appl. No. 10/447,526, filed May 29, 2003.

Vadimovich G.A., et al., "A Method of Endoscopic Investigation of Vascular Structures Directly Through Flowing Blood," The Heart Surgery Forum, 1999, vol. 2 (2), pp. 136-138.

Written Opinion for Application No. PCT/US2004/032374, dated May 13, 2005, 8 pages.

Yamamoto N., et al., "Nonfluoroscopic Guidance for Catheter Placement into the Coronary Sinus Under Direct Vision Using a Balloon-Tipped Cardioscope," Pacing and Clinical Electrophysiology, 1998, vol. 21 (9), pp. 1724-1729.

\* cited by examiner

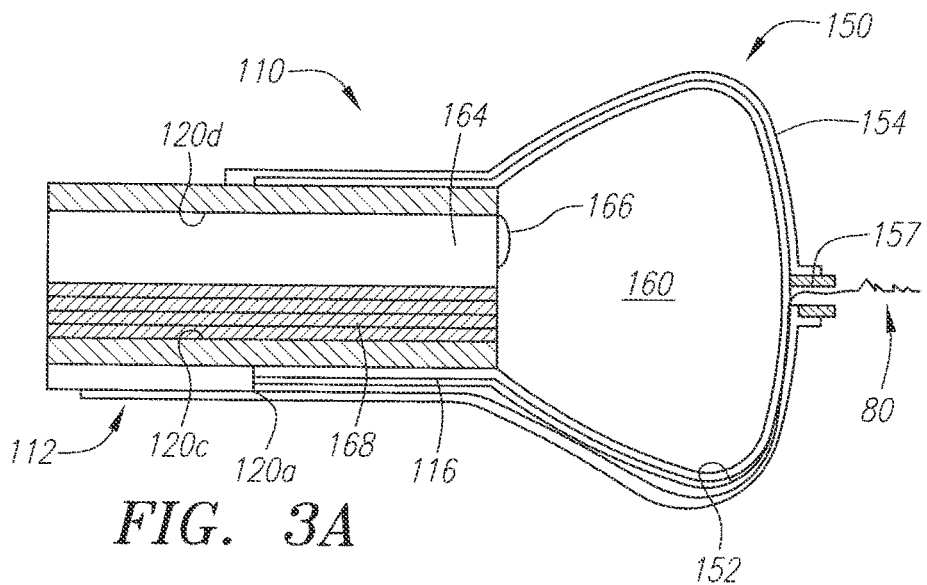
FIG. 3A
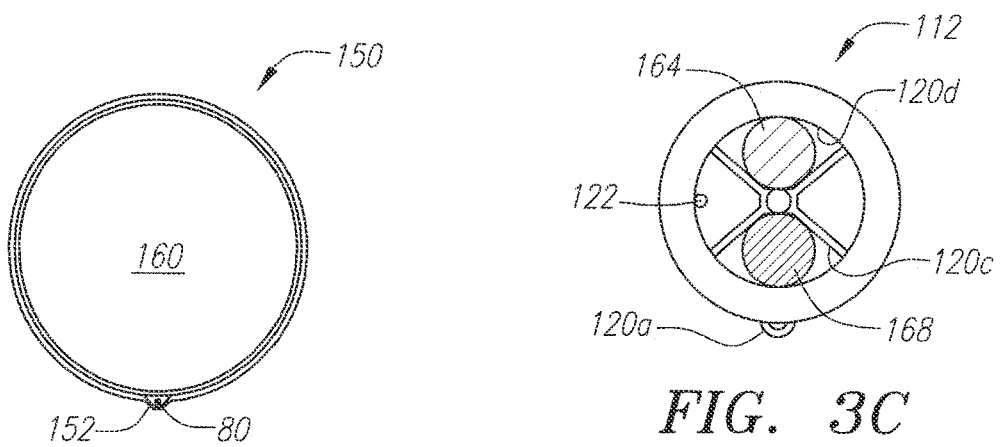
FIG. 3B
FIG. 3C
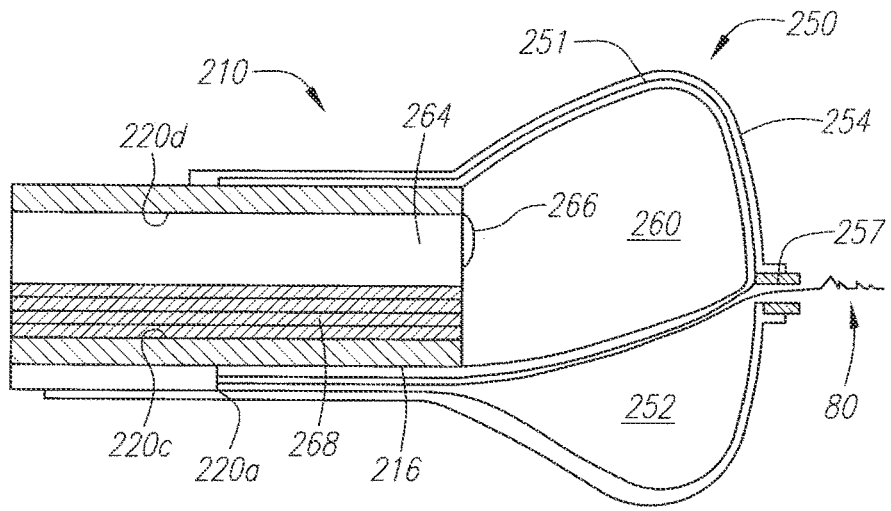
FIG. 4

CATHETER SYSTEMS WITH IMAGING ASSEMBLIES

This application is a continuation of U.S. Ser. No. 17/345,768, filed Jun. 11, 2021, which is a continuation of U.S. Ser. No. 16/459,504, filed Jul. 1, 2019, which is a continuation of U.S. Ser. No. 15/175,601, filed Jun. 7, 2016, which is a continuation of U.S. Ser. No. 14/591,278, filed Jan. 7, 2015, which is a divisional of U.S. Ser. No. 11/465,123, filed Aug. 16, 2006, which is a continuation-in-part of U.S. Ser. No. 11/379,562, filed Apr. 20, 2006, which is a continuation-in-part of application Ser. No. 11/269,976, filed Nov. 8, 2005, which is a division of application Ser. No. 10/447,526, filed May 29, 2003, now U.S. Pat. No. 6,979,290, which claims benefit of provisional application Ser. No. 60/384,262, filed May 30, 2002. U.S. Ser. No. 11/465,123 claims benefit of provisional application Ser. No. 60/708,747, filed Aug. 16, 2005. The disclosures of each of these references is expressly incorporated by reference herein.

FIELD OF THE INVENTION

The present invention relates generally to apparatus and methods for delivering leads into a patient's body, and, more particularly, to apparatus and methods for delivering leads within body lumens of a heart and/to epicardial locations under direct visualization.

BACKGROUND

Minimally invasive procedures have been implemented in a variety of medical settings, e.g., for vascular interventions, such as angioplasty, stenting, embolic protection, electrical heart stimulation, heart mapping and visualization, and the like. One such procedure involves delivering an electrical lead into a coronary vein of a patient's heart that may be used to electrically stimulate the heart.

During such procedures, instruments, fluids, and/or medicaments may be delivered within a patient's vasculature using visualization tools, such as x-ray, fluoroscopy, ultrasound imaging, endoscopy, and the like. In many procedures, it may be desired to deliver instruments through opaque fluids, such as blood, or other materials. Endoscopes have been suggested that include devices for displacing these materials from an optical path, e.g., by introducing a clear fluid from the endoscope in an attempt to clear its field of view. Yet there are still improvements that may be made to such devices.

Accordingly, apparatus and methods for imaging within body lumens and/or for delivering instruments and/or fluids into a patient's body would be useful.

SUMMARY OF THE INVENTION

The present invention is directed to apparatus and methods for delivering leads into a patient's body, and, more particularly, to apparatus and methods for securing leads relative to tissue structures and/or body lumens or cavities, and for delivering leads within body lumens of a heart and/to epicardial locations under direct visualization.

In accordance with one aspect of the present invention, a system is provided for delivering a lead into a body cavity of a patient that includes an imaging device, an elongate rail, and a lead. The imaging device may include a proximal end, a distal end sized for introduction into a body cavity. The elongate rail may include a proximal end, a distal end sized for introduction into a body cavity, and one or more fixation elements on the distal end for securing the distal end to a delivery location within a body cavity. The elongate rail may be sized for introduction through a lumen of the imaging device, e.g., a guidewire. Alternatively, the elongate rail may be sized to be introduced around the imaging device, e.g., a sheath or other tubular member.

In one embodiment, the lead may include a proximal end, a distal end, and a lumen extending therebetween for receiving the elongate rail therein, such that the lead may be advanced over the elongate rail. In another embodiment, the lead may include a proximal end, and a distal end sized for introduction through a lumen of the elongate rail. The lead may include one or more electrodes on the distal end, e.g., for pacing or other electrical stimulation of the heart.

In accordance with another embodiment, a method is provided for delivering a lead within a body cavity. A distal end of an imaging device may be placed against a wall of a tissue structure adjacent a body cavity, and manipulated relative to the wall of the tissue structure to image and/or otherwise identify a target site. A distal end of an elongate rail may be delivered via the imaging device, e.g., through or over the imaging device, to the target site, and secured relative to the target site. For example, the distal end may include one or more fixation elements for securing the distal end to tissue at the target site.

The imaging catheter may be removed, and then a lead may be advanced via the elongate rail, e.g., over or through the elongate rail, to the target site, and secured relative to the target site. For example, the distal end of the lead may include one or more fixation elements for securing the distal end to tissue at the target site. The elongate rail may remain or may then be removed. In an alternative embodiment, the lead may be secured to the elongate rail, thereby securing the lead relative to the target site.

In accordance with still another embodiment, a method is provided for delivering a lead within a body cavity. An imaging catheter may be introduced through one or more body lumens, and used to identify a delivery location for a lead. A distal end of an elongate rail may be introduced via the imaging catheter to the identified delivery location, and secured at the delivery location. A lead may be delivered via the rail to the delivery location, and secured relative to the delivery location. For example, the delivery location may be a location in the right ventricular septum or at another location within a chamber of a heart.

In accordance with yet another embodiment, a method is provided for delivering a medical device within a body cavity. An imaging device may be introduced into a thoracic cavity adjacent a heart of a patient. A surface of the heart may be imaged using the imaging catheter to identify a delivery location for a lead. A distal end of an elongate rail may be introduced via the imaging catheter to the delivery location, and secured to the delivery location, e.g., to epicardial tissue of the heart. A lead may be delivered via the elongate rail to the delivery location, secured relative to the delivery location.

Other objects and features of the present invention will become apparent from consideration of the following description taken in conjunction with the accompanying drawings.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 3A is a cross-sectional detail, showing an alternative embodiment of an apparatus for cannulating a body lumen including a balloon, in accordance with the present invention.

FIGS. 3B and 3C are cross-sections of the apparatus of FIG. 3A, taken along lines 3B-3B, and 3C-3C, respectively.

FIG. 4 is a cross-sectional detail, showing another alternative embodiment of an apparatus for cannulating a body lumen including a balloon, in accordance with the present invention.

DETAILED DESCRIPTION

Figure 1A:
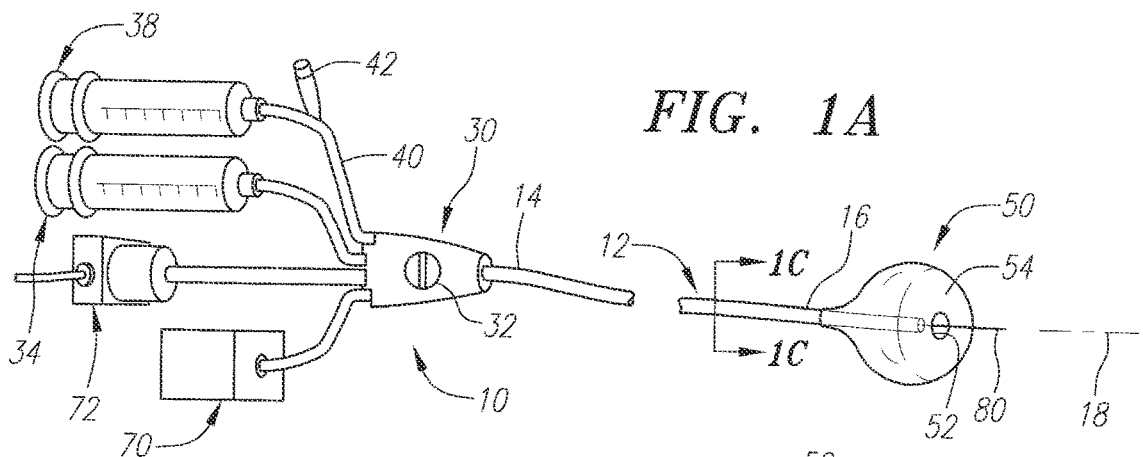
FIG. 1A is a perspective view of a first preferred embodiment of an apparatus for cannulating a body lumen, in accordance with the present invention.
Figure 1B:
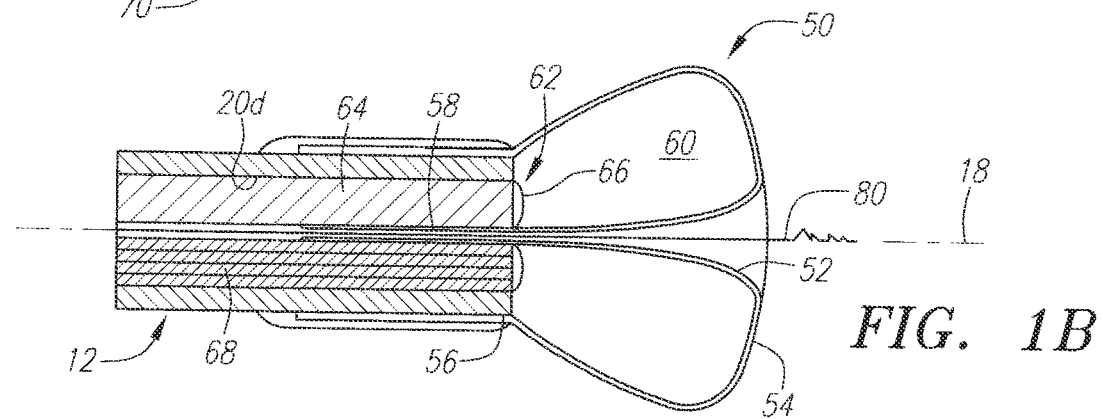
FIG. 1B is a cross-sectional detail of a distal end of the apparatus of FIG. 1A, showing a guidewire inserted through the apparatus.
Figure 1C:
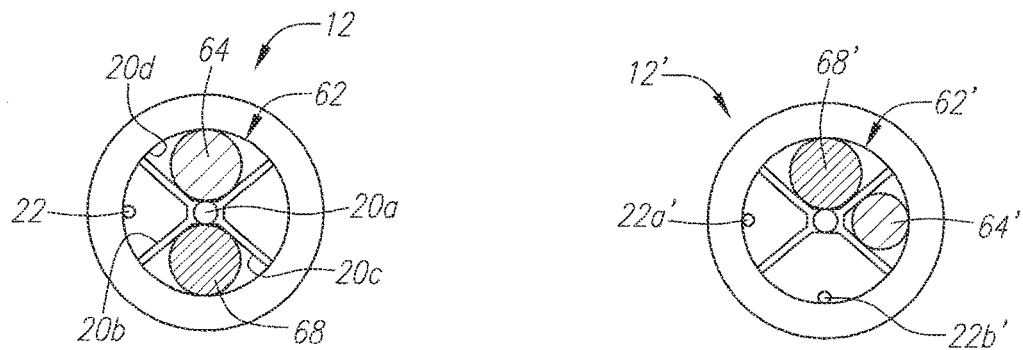
FIG. 1C is a cross-section of the apparatus of FIG. 1A, taken along line 1C-1C.

Turning to the drawings, FIGS. 1A-1C show a first preferred embodiment of an apparatus 10 for imaging a body lumen, e.g., for visualizing, accessing, and/or cannulating a body lumen or tissue structure from a body cavity (not shown). In an exemplary embodiment, as explained further below, the apparatus 10 may be used for imaging a wall of a right atrium of a heart, e.g., for visualizing, accessing, and/or cannulating a coronary sinus ostium, although the apparatus 10 may be used for visualizing, accessing, and/or cannulating other body lumens and/or tissue structures as well. Generally, as shown in FIG. 1A, the apparatus 10 may include a catheter or other elongate member 12, a balloon or other expandable member 50 on a distal end 16 of the catheter 12, and an imaging assembly 62 carried by the distal end 16 of the catheter 12 for imaging through the balloon 50.

The catheter 12 generally is an elongate tubular body including a proximal end 14, a distal end 16 having a size and shape for insertion into a patient's body, and a central longitudinal axis 18 extending between the proximal and distal ends 14, 16. The catheter 12 may include one or more lumens 20 also extending between the proximal and distal ends 14, 16, e.g., a cannulation lumen 20a, an inflation lumen 20b, and one or more lumens 20c, 20d (best seen in FIG. 1C) for the imaging assembly 62.

The catheter 12 may be substantially flexible, semi-rigid, and/or rigid along its length, and may be formed from a variety of materials, including plastic, metal, and/or composite materials, as is well known to those skilled in the art. For example, the catheter 12 may be substantially flexible at the distal end 16 to facilitate advancement through tortuous anatomy, and/or may be semi-rigid or rigid at the proximal end 14 to enhance pushability of the catheter 12 without substantial risk of buckling or kinking.

Figure 2B:
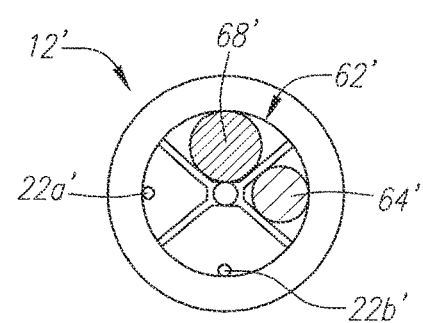
FIG. 2B is a cross-section of the apparatus of FIG. 2A, taken along line 2B-2B.
Figure 2A:
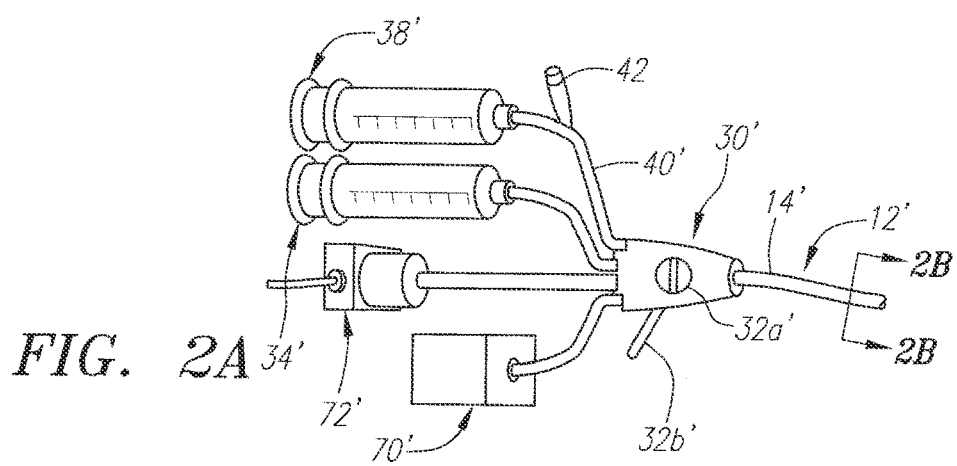
FIG. 2A is a perspective view of an alternative embodiment of the apparatus of FIG. 1A, having two degrees of steering.

Preferably, the catheter 12 is steerable, i.e., the distal end 16 may be controllably deflected transversely relative to the longitudinal axis 18. In the embodiment shown in FIGS. 1A-1C, a single pullwire or other steering element 22 may be provided, e.g., within one of the lumens 20, for steering the distal end 16 of the catheter 12 in one transverse plane (thereby providing one degree of freedom). Alternatively, in another embodiment, such as that shown in FIGS. 2A and 2B, two pullwires 22' may be provided for steering the distal end 16' of the catheter 12' in two orthogonal planes (thereby providing two degrees of freedom).

The pullwire(s) 22 may be a cable, wire, band, and the like that may be slidably disposed within a lumen, such as the inflation lumen 20b shown in FIG. 1C. The pullwire(s) 22 may be attached or otherwise fixed relative to the catheter 12 at a location adjacent the distal end 16, preferably offset radially outwardly from the central axis 18. Thus, when the pullwire 22 is pulled proximally, e.g., from the proximal end 14 of the catheter 12, a bending force may be applied to the distal end 16, causing the distal end 16 to bend transversely relative to the central axis 18.

The catheter 12 may also include a handle or other control mechanism 30 coupled to or otherwise provided on the proximal end 14 of the catheter 12. The handle 30 may include one or more steering controls 32 that may be actuated to steer the distal end 16 of the catheter 12. For example, as shown in FIG. 1, a dial 32 may be provided that may be coupled to the pullwire 22. The dial 32 may be rotated to apply a proximal force on the pullwire 22, thereby bending the distal end 16 of the catheter 12. In a further alternative, the steering control 32 may include a slider coupled to a pullwire (not shown) such that translation of the slider translates the pullwire, causing deflection of the distal tip of the catheter 12 as the pullwire is placed in tension or compression. Exemplary embodiments of steering controls are disclosed in application Ser. No. 11/062,074, filed Feb. 17, 2005, the entire disclosure of which is expressly incorporated by reference herein.

The handle 30 may also include ports and/or other connections for connecting other components to the catheter 12. It will be appreciated that any known connectors may be provided for permanently or temporarily connecting components to the catheter 12. For example, a leer lock connector may be used to connect tubing or other fluid-conveying components to the handle 30.

As shown in FIG. 1A, a syringe or other source of fluid 34, e.g., including saline, carbon dioxide, nitrogen, or air, may be connected via tubing 36 to the inflation lumen 20*b* (not shown, see FIG. 1C) for inflating the balloon 50. In addition or alternatively, a stop-cock or check valve (not shown) may be included in the path of the inflation lumen 20*b* to selectively maintain balloon inflation. For example, a luer-activated check valve may be used, such that a leer-lock syringe 34 may be engaged with the apparatus 10 to open the valve for balloon inflation or deflation. When the syringe 34 is removed, the check valve may automatically close to maintain balloon inflation. The syringe 34 may also provide a source of vacuum for deflating the balloon 50, as is known in the art. Another source of fluid 38, e.g., saline, and/or a therapeutic or diagnostic agent, may be connected via tubing 40 to the cannulation lumen 20*a* for delivering fluid beyond the distal end 16 of the catheter 12.

In addition, an access port 42 may also communicate with the cannulation lumen 20*a*, e.g., including a hemostatic seal and the like (not shown), for delivering one or more instruments (such as guidewire 80, shown in FIG. 1B) through the cannulation lumen 20*a*, as explained further below. Optionally, the handle 30 may include a shape, size, and/or contour (not shown) for facilitating manipulating the catheter 12 during use.

Returning to FIGS. 1A and 1B, a substantially transparent balloon 50 may be provided on the distal end 16 of the tubular member 12. The balloon 50 may be expandable from a contracted condition (not show to an enlarged condition when fluid is introduced into an interior 60 of the balloon 50. In the embodiment shown, a channel 52 may extend through the balloon 50 that communicates with a lumen 20 of the catheter 12, e.g., the cannulation lumen 20*a*. Preferably, the channel 52 extends through the balloon 50 concentrically with the central axis 18, as best seen in FIG. 1B.

In an exemplary embodiment, the balloon 50 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 50 may expand to a predetermined shape when fully inflated to the enlarged configuration. Preferably, in the enlarged configuration, the balloon 50 may have a distal surface 54 that is substantially flat or otherwise configured for contacting a wall of a body cavity, such as the right atrium(not shown). Alternatively, as shown in FIGS. 19A and 19B, an apparatus 710 may be provided that carries a balloon 750 having a frustoconical shape and/or a convex distal surface 754.

The material may be sufficiently flexible and/or elastic such that the distal surface 54 may conform substantially to the wall of the body cavity. Preferably, the balloon 50 is also sufficiently noncompliant to displace blood or other fluid from between the distal surface 54 and the wall of the body cavity to facilitate imaging the wall through the balloon 50, as explained further below. Alternatively, the balloon 50 may be formed from compliant and/or elastomeric materials, such as silicone, latex, isoprene, and chronoprene.

In the exemplary embodiment shown in FIG. 1B, the balloon 50 may be formed from one or more panels that may be attached to one another, e.g., using an adhesive (such as an adhesive cured using ultraviolet ("UV") light), sonic welding, and/or heating, after lapping or butting adjacent panels together. Alternatively, the balloon 50 may be molded around or within a mold (not shown) having a desired shape for the balloon 50 in the enlarged condition.

The resulting balloon 50 may include a proximal end 56 that may be attached to an outer surface of the catheter 12, e.g., using an adhesive, heating, sonic welding, an interference fit, and/or an outer sleeve. The channel 52 may be formed from the same material as the rest of the balloon 50, and a proximal end 58 of the channel may be attached to the distal end 16 of the catheter 12, e.g., within or concentric with the cannulation lumen 20*a*. Alternatively, the channel may be formed from a semi-rigid or rigid tubular member, as shown in FIGS. 6-10, and described further below.

In another alternative, the channel 52 may be formed of one or more materials to provide a stiffness transition or multiple transitions. In a further alternative, the channel 52 may be flexible or semi-flexible, but also biased and/or constrained in on or more directions, e.g., to avoid or minimize deflection of the channel 52 into a position that may obscure the field of view beyond the apparatus 10. In still another alternative, the channel 52 may be transparent or semi-transparent to light in the spectra used for imaging, e.g., to facilitate visualization of devices, instruments, agents, and/or fluids passing through the tubular member. Alternatively, the channel 52 may be replaced or reinforced with any suitable stiffening element such as a wire, spring, composite element, plastic element, and the like.

As best seen in FIG. 1B, the interior 60 of the balloon 50 may have a generally annular shape that preferably communicates with the inflation lumen 20*b* (not shown, see FIG. 1C) of the catheter 12. Substantially transparent inflation media, e.g., saline, carbon dioxide, nitrogen, air, and the like, may be introduced into the interior 60 of the balloon 50 to expand the balloon 50 towards the enlarged condition shown in FIGS. 1A and 1B. As used herein, "transparent" refers to any material and/or fluid that may permit sufficient light to pass therethrough in order to identify or otherwise visualize objects through the material and/or fluid. "Light" as used herein may refer to light radiation within the visible spectrum, but may also include other spectra, such as infrared ("IR") or ultraviolet ("UV") light.

Alternatively, the balloon and/or channel may have different configurations, such as that shown in FIGS. 3A-3C and 4. For example, as shown in FIGS. 3A-3C, an apparatus 110 is shown that includes a catheter 112 that may include one or more lumens, e.g., lumens 120*c*, 120*d* for receiving components of an imaging assembly 162 therethrough, similar to the previous embodiment. Unlike the previous embodiment, a cannulation lumen 120*a* extends along an outer surface of the catheter 112 that extends between a proximal end (not shown) to a distal end 116 of the catheter 112. The lumen 120*a* may be a separate tubular member attached to the catheter 112 or may be an integral part of the catheter 112, e.g., formed as a single extrusion.

A balloon 150 may be carried on the distal end 116 of the catheter 112 that defines an interior 160 communicating with an inflation lumen (not shown) that extends to the proximal end of the catheter 112, similar to the previous embodiment. A channel 152 may extend along a wall of the balloon 150 that communicates with the cannulation lumen 120*a*. The channel 152 may be defined by a panel of material attached to the balloon 150, similar to the materials and methods for making balloon 50, as described above. Alternatively, an inner balloon panel may be provided within an outer balloon panel and the panels may be attached to one another, e.g., along one or more seams defining the channel 152.

A nipple or annular collar 157 may be provided on the distal surface 154 of the balloon 150, e.g., to guide a guidewire 80 or other instrument out of the balloon 150, and/or to stabilize the device relative to a body lumen or other tissue structure (not shown). Thus, a guidewire 80 may be inserted into the cannulation lumen 120*a* from the proximal end of the catheter 112, the channel 152 guiding the guidewire 80 through the balloon 150 until it exits through the nipple 157 to a location beyond the distal surface 152 of the balloon 150.

In another alternative, shown in FIG. 4, an inner balloon 251 may be provided within an interior 260 of an outer balloon 250. The inner balloon 251 may be expandable to a size and/or shape that is smaller than the outer balloon 250, thereby defining a channel 252 between the balloons 251, 252. Thus, a guidewire 80 or other instrument (not shown) may be inserted into a cannulation lumen 220*a*, e.g., extending along an outer surface of the catheter 212. The guidewire 80 may enter the channel 252 between the balloons 251, 252 until it exits through a nipple 257, similar to the embodiment shown in FIGS. 3A-3C.

Figure 5A:
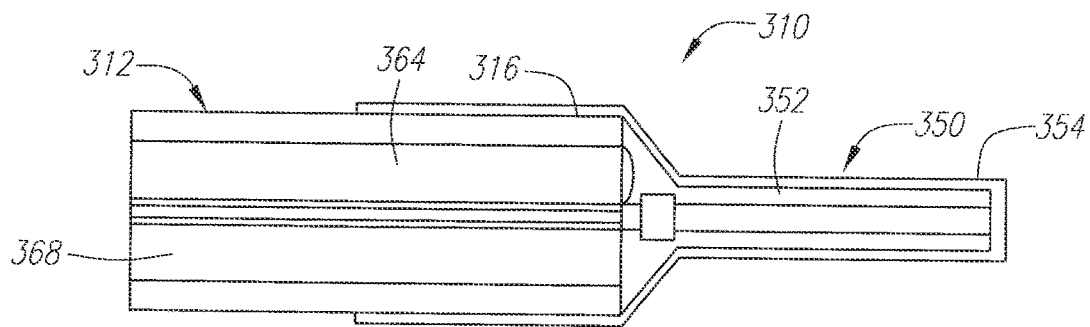
FIGS. 5A-5C are cross-sectional side views of an embodiment of a mechanically expandable member that may be substituted for an inflatable balloon in an apparatus, in accordance with the present invention.
Figure 5B:
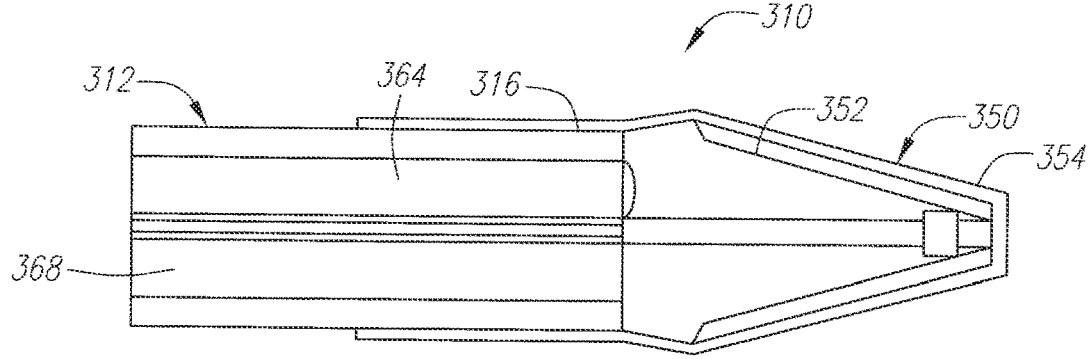
Figure 5C:
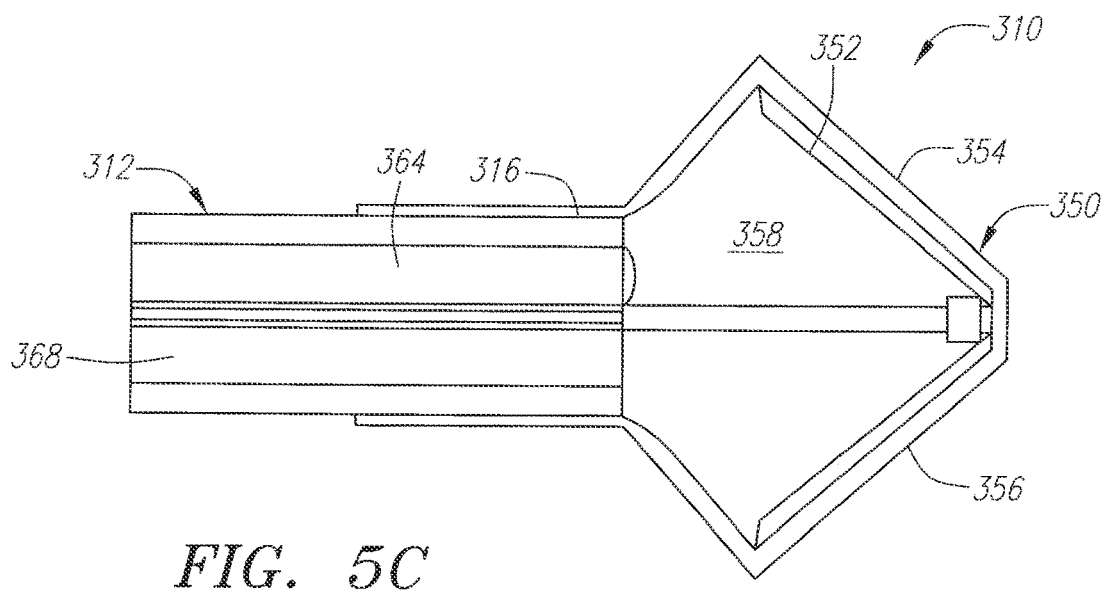

In yet another alternative, shown in FIGS. 5A-5C, an apparatus 310 may be provided that includes a mechanically expandable member 350 carried on a distal end 316 of a catheter 312. A frame 352 may be coupled to the distal end 316 that may support a substantially transparent, flexible membrane 354. The frame 352 may include a plurality of members that are movable away from and towards one another, thereby causing the membrane 354 to move between contracted and enlarged conditions. Alternatively, the frame 352 may be constructed of plastic or wire mesh, or of a laser cut expandable framework.

The frame 352 may be actuated from a proximal end (not shown) of the catheter 312, e.g., to cause the frame 352 to expand radially outwardly, as shown in FIGS. 5B and 5C, As the frame 352 expands, the membrane 354 may provide a substantially transparent surface 356 through which an optical imaging assembly, e.g., including an optical fiber bundle 364 and/or a light guide 368, similar to that described further below, may obtain optical images. Optionally, an interior 358 of the membrane 354 may be filled with a substantially transparent fluid, similar to the balloons described above, to facilitate imaging through the expandable member 350.

Returning to FIGS. 1A-1C, the imaging assembly 62 generally includes an optical imaging element 64 that is exposed within the interior 60 of the balloon 50 for capturing light images through the balloon 50. In one embodiment, the optical imaging element comprises an image sensor such as a CCD, CMOS, and the like disposed distally, e.g., adjacent or within the distal end 16. In another embodiment, the optical imaging element 64 may include a bundle of optical fibers, e.g. a coherent image bundle, that extends between the proximal and distal ends 14, 16 of the catheter 12, e.g., through the lumen 20*d*, as shown in FIG. 1C. The fiber bundle 64 may include about ten thousand (10,000) optical fibers, although it may include between about one and fifty thousand (1,000-50,000) fibers in order to provide a desired resolution in the images obtained by the fiber bundle 64.

A lens 66, e.g., a GRIN or self-oc lens, may be coupled to the fiber bundle 64 in order to focus light from beyond the distal surface 54 of the balloon 50 onto the fiber bundle 64 in order to generate a resolved image at the proximal end of the fiber bundle 64, as is well known to those skilled in the art. Optionally, a directional prism or other optical element (not shown) may be provided for directing a field of view of the fiber bundle 64 as desired, as explained further below. In order to decrease the tendency of bubbles to adhere to the distal surface of a distal lens or other optical element (not shown), the lens may be coated with a hydrophilic coating, or designed such that its geometry or the surrounding catheter geometry decreases the tendency of bubbles to adhere, e.g., by providing a convex exposed surface. Other features, such as directed flushing, may be employed to dislodge any adhered bubbles during use.

In addition, the imaging assembly 62 may include one or more light sources disposed at the distal end 16 of the catheter 12. For example, the light sources may be one or more light emitting diodes. Alternatively, the imaging assembly 62 may include one or more light guides 68 carried by the distal end 16 of the catheter 12 for delivering light into the interior 60 and/or through the distal surface 54 of the balloon 50. Although a single light guide 68 is shown in FIGS. 1B and 1C, it will be appreciated that a plurality of light guides (not shown) may be provided in a common lumen or separate lumens (also not shown) within the catheter 12. The light guide(s) 68 may include a plurality of optical fibers, e.g., formed from acrylic and the like, that may extend to the proximal end 14 of the catheter 12. As shown in FIG. 1A, a source of light 70 may be coupled to the light guide(s) 68, e.g., via the handle 30, for delivering light through the light guide(s) 68 and into the balloon 50.

A device 72 may be coupled or otherwise provided at the proximal end 14 of the apparatus 10 for acquiring and/or capturing images obtained by the optical imaging assembly 62. For example, one or more lenses (not shown) may be coupled to the fiber bundle 64 for focusing and/or resolving light passing through the fiber bundle 64, e.g., to pass the image to the device 72. The device 72 may include a CCD, CMOS, and/or other device, known to those skilled in the art, e.g., to digitize or otherwise convent the light images from the fiber bundle 64 into electrical signals that may be transferred to a processor and/or display (not shown).

For example, a computer (not shown) may be coupled to the device 72, (see FIG. 1A), e.g., by a cable (not shown). Alternatively, instead of the computer, other display or capture devices may be coupled to the device 72, such as a laptop computer, handheld or PDA device, a computer terminal, a LCD display, standard video monitor, and the like (not shown), to display and/or store the images acquired from the fiber bundle 64. Optionally, the computer (or other capture device) may provide electrical power to the device 72, light source 70, and/or other components of the apparatus 10.

For a cable connection between the device 72 and the computer, various protocols may be used, such as USB, Firewire, standard video signal protocols, and the like. Alternatively, the computer may be coupled to the device 72 via a wireless connection, for example, including one or more transmitters and/or receiving using radio frequency signals, Bluetooth, infrared links, and the like.

Optionally, the apparatus 10 may include additional data acquisition features, such as a microphone (not shown), e.g., allowing procedure notes to be dictated during an imaging procedure or allowing the apparatus 10 and/or computer 10 to be controlled by voice commands. In addition or alternatively, drivers and/or software may be stored on a memory chip (not shown) in the apparatus 10 that may be uploaded to the computer when connected to the apparatus 10. When a complex interface is used to connect the apparatus 10 to the computer or other display device, the apparatus 10 and/or the computer may be capable of disabling the complex interface and enable simple video output.

Turning to FIGS. 6-10, another preferred embodiment of an apparatus 410 is shown for visualizing and/or cannulating a body lumen. Similar to the previous embodiments, the apparatus 410 generally includes a catheter 412, a balloon 450 carried by the catheter 412, and an imaging assembly 462 for imaging through the balloon 450.

Also, similar to the previous embodiments, the catheter 412 may be an elongate tubular body including a proximal end 414, a distal end 416, and a central longitudinal axis 418 extending therebetween. The catheter 412 may be substantially flexible, semi-rigid, and/or rigid along its length, and may be formed from a variety of materials, including plastic, metal, and/or composite materials. The catheter 412 may have a diameter between about five and ten French (1.67-3.33 mm), and preferably between about six and eight French (2.00-2.67 mm).

The catheter 412 may include one or more lumens 420 also extending between the proximal and distal ends 414, 416, e.g., a cannulation lumen 420a, an inflation lumen 420b, and one or more lumens 420c-f for the imaging assembly 462 and/or one or more pullwires or other steering elements 422. In addition, the catheter 412 may include a handle (not shown) and/or other components, e.g., sources of fluid, a light source, an image capture device, and the like (also not shown) on the proximal end 414, similar to the other embodiments described herein.

Preferably, the catheter 412 includes multiple extrusions that are attached to one another to provide a desired length. For example, the catheter 412 may include a proximal portion 412a having a first cross-section, shown in FIGS. 8A and 8B, and a distal portion 412b having a second cross-section, shown in FIG. 8C. The proximal portion 412a may have a length between about nine and thirty six inches (22-90 cm), and preferably between about eighteen and twenty eight inches (45-70 cm).

The proximal portion 412a preferably includes three lumens, a cannulation lumen 420a, an inflation lumen 420b, and an accessories lumen 420c. The cannulation lumen 420a may provide a path for a guidewire or other instrument, fluid, and the like to pass between the proximal and distal ends 414, 416 of the catheter 412. Optionally, a tube 424, e.g., made from polyamide and the like, may be provided within the cannulation lumen 420a, e.g., to reinforce the cannulation lumen 420a and/or catheter 412. The inflation lumen 420b may communicate with an interior 460 of the balloon 450, similar to the previous embodiments, for delivering substantially transparent inflation media into the balloon 450. The accessories lumen 420c may carry a plurality of components, e.g., an optical imaging (fiber optic) bundle 464, pull-wire 422, and/or a set of light guides 468, similar to the previous embodiments described above.

Figure 7A:
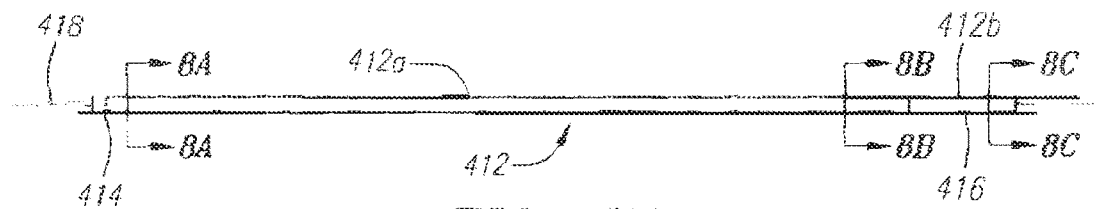
FIG. 7A is a side view of a catheter that may be included in the apparatus of FIG. 6.
Figure 7B:
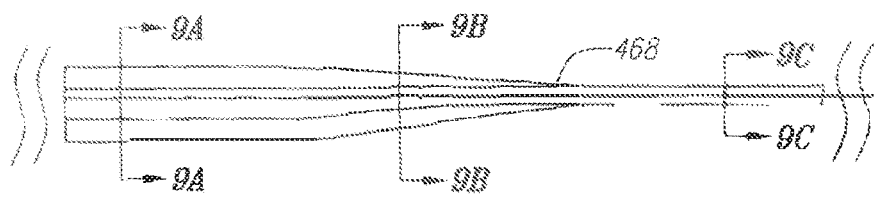
FIG. 7B is a side view detailing a set of light guides that may be included in the catheter of FIG. 7A.
Figure 8A:
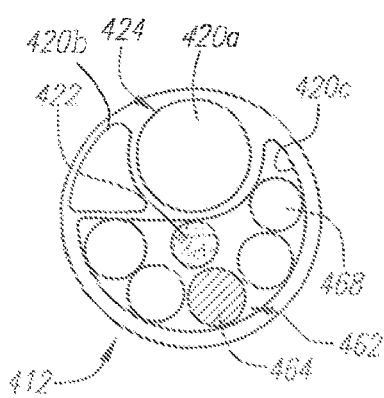
FIGS. 8A-8C are cross-sections of the catheter of FIG. 7, taken along lines 8A-8A, 8B-8B, and 8C-8C, respectively.
Figure 8B:
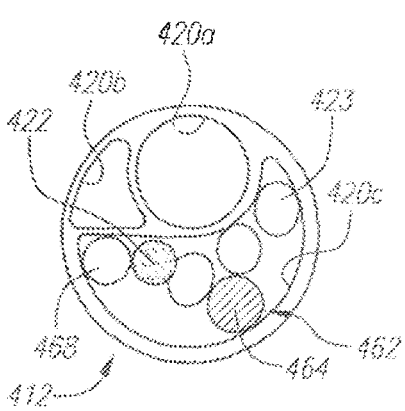
Figure 8C:
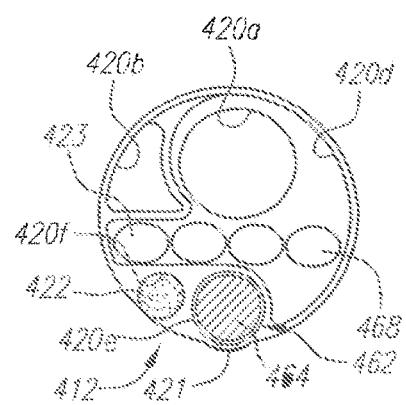
Figure 9A:
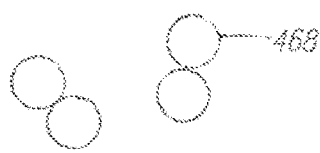
FIGS. 9A-9C are cross-sections of the light guides of FIG. 7B, taken along lines 9A-9A, 9B-9B, and 9C-9C, respectively.
Figure 9B:
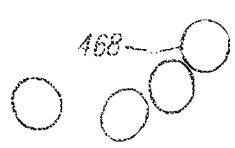
Figure 9C:
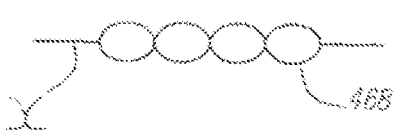

With reference to FIGS. 7A and 8C, the distal portion 412b may have a length between about 25.4-101.6 millimeters (mm), and preferably between about 50.8-76.2 millimeters (mm). The distal portion 412b may be substantially permanently attached to the proximal portion 412a, e.g., using a lap or butt joint, and/or an adhesive, interference fit, heating, and/or sonic welding. The distal portion 412b may include continuations of the cannulation lumen 420a and inflation lumen 420b from the proximal portion 412a. In addition, the distal portion 412b may include a light guide lumen 420d, a fiber optic lumen 420e, and a pullwire lumen 420f that may communicate with the accessories lumen 420c when the proximal and distal portions 412a, 412b are attached to one another.

Preferably, the fiber optic lumen 420e is located as far away from the cannulation lumen 420a as possible in order to maximize a field of view of the fiber bundle 464 received therein. For example, as shown in FIG. 8C, the distal portion 412b may include a ridge 421 extending axially along an outer surface of the distal portion 412b, thereby maximizing a distance that the fiber optic lumen 420e may be disposed away from the cannulation lumen 420a. When the fiber bundle 464 is inserted into the catheter 412, the fiber bundle 464 may be received in the fiber optic lumen 420e in the distal portion 412b, and in the accessories lumen 420c in the proximal portion 412a. The fiber bundle 464 may be secured at one or more locations within the lumens 420e, 420c, e.g., using an adhesive and the like. Thus, the location of the fiber bundle 464 may be fixed in the distal portion 412b to stabilize its field of view relative to the catheter 412.

The pullwire lumen 420f may also be located as far away from the central axis 418, e.g., due to another ridge extending the outer surface. This arrangement may maximize a bending force applied to the catheter 412 when the pullwire 422 is pulled proximally.

Turning to FIGS. 7B and 9A-9C, the set of light guides 468 may be received in the accessories lumen 420c in the proximal portion 412a and in the light guide lumen 420d in the distal portion 412b. The set of light guides 468 may include between about one and twenty five, and preferably between about four and ten, elongate light guides. Each of the light guides 468 may be formed from a substantially transparent acrylic fiber or other light transmitting material, e.g., having a diameter between about twenty five micrometers and one millimeter (25 µm-1 mm), and preferable between about two hundred fifty and five hundred micrometers (250-500 µm).

At the proximal end 414 of the catheter 412, the light guides 468 may be substantially cylindrical, while towards the distal end 416 of the catheter 412, the light guides 468 may be tapered and/or flattened. For example, the light guides 468 may taper within a few inches of the proximal end 414 of the catheter 412, preferably reducing an overall cross-section of the light guides 468 by as much as fifty percent (50%). The light guides 468 may be disposed loosely within the accessories lumen 420c of the proximal portion 412a.

The enlarged size of the light guides 468 at the proximal end 414 of the catheter 412 may facilitate connecting the light guides 468 to a light source (not shown), as will be appreciated by those skilled in the art. Optionally, exposed lengths (not shown) of the light guides 468 beyond the proximal end 414 of the catheter 412 may be further enlarged to facilitate such connections. For example, if the light guides 468 are acrylic fibers, heat may be applied, e.g., up to one hundred seventy degrees Fahrenheit (170° F.), to cause the light guides 468 to shorten. The acrylic material may increase in diameter as it shortens, thereby increasing the diameter of the light guides 468 by as much as three times as they shorten. This may allow the light guides 468 to be columnated and connected to a light source without requiring a lens (not shown).

As the light guides 468 transition from the proximal portion 412a to the distal portion 412b, they may be linearly aligned and/or secured to each other, e.g., using an epoxy or other adhesive, and/or by reflowing the fiber material, such that surfaces of adjacent fibers are bonded at adjacent contact points. To align the light guides 468 in a desired orientation within the distal portion 412b, the light guides 468 may be received in an axial ridge or slot 423 within the distal portion 412b, as shown in FIG. 8C.

The bonded array of light guides 468 may provide a hinge, i.e., biasing the distal portion 412b of the catheter 412 to bend in a predetermined direction. Specifically, the light guides 468 may provide a higher bending moment along a bond axis "x" (shown in FIG. 9C), while exhibiting a much lower bending moment along an axis orthogonal to the bond axis "x." As the pullwire 422 is pulled proximally, the force may be transferred to the distal portion 412b of the catheter 412. Because of the asymmetric bending moments created by the light guides 468, the distal portion 412b of the catheter 412 may bend in one plane orthogonal to the bond axis "x," i.e., towards the pullwire 422, while resisting bending along the bond axis "x." This may cause the catheter 412 to curve from a location where the pullwire 422 transitions from being located at the center of the catheter 412 (e.g., as shown in FIG. 8A) to a location on the distal end 416 where the pull wire 422 is fixed (e.g., as shown in FIG. 8C).

Figure 10:
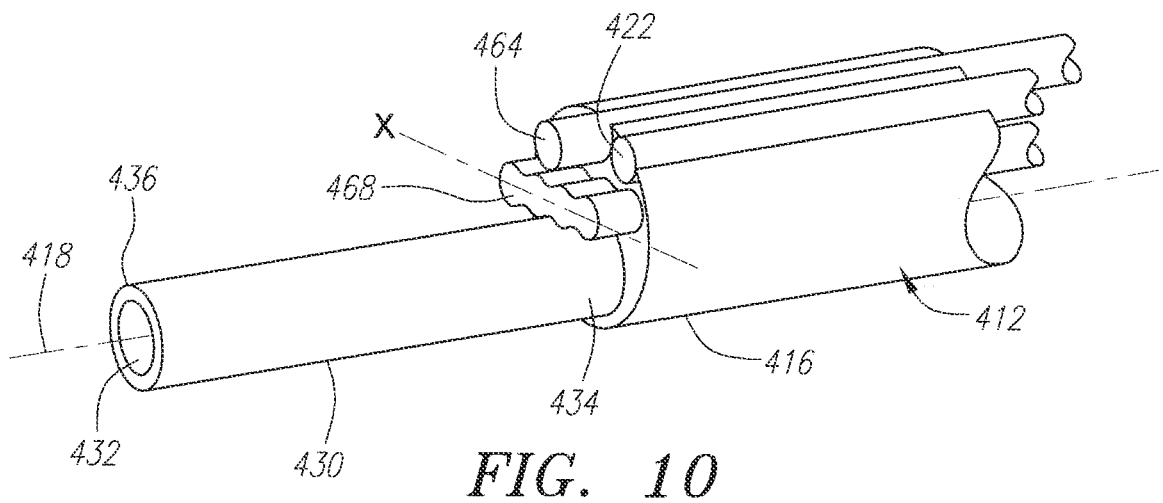
FIG. 10 is a perspective detail of the apparatus of FIGS. 6 and 7A, with the balloon omitted for clarity.
Figure 11A:
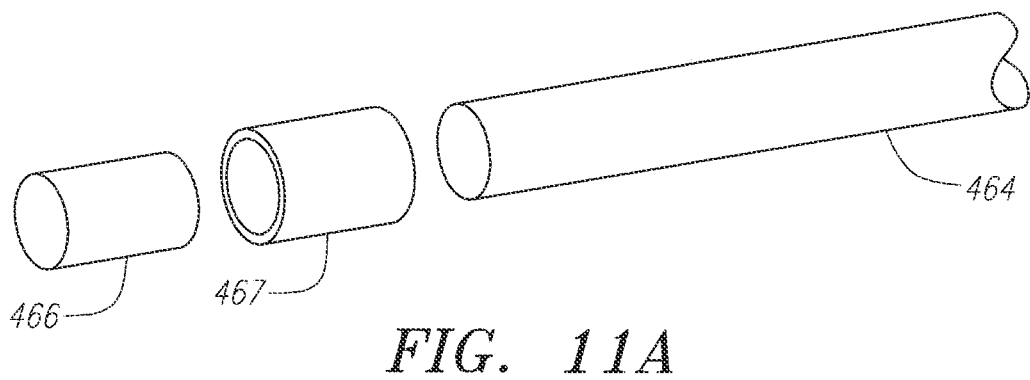
FIGS. 11A and 11B are exploded and perspective views of a optical fiber bundle having a lens attached thereto.
Figure 11B:
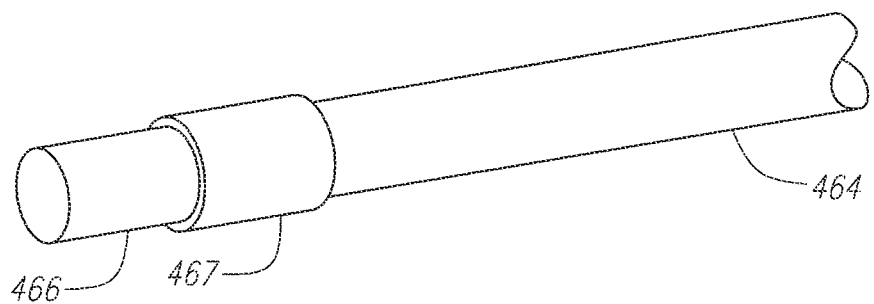

Turning to FIGS. 10-11B, a bundle 464 of optical fibers may be provided, similar to the embodiments described above. Preferably, a lens 466 is coupled to the fiber bundle 464, e.g., a GRIN or self-oc lens, as described above. For example, as shown in FIGS. 11A and 11B, a sleeve 467, e.g., shrink wrap and the like, may be provided that may be secured around the lens 466 and the optical imaging bundle 464. Optionally, a fluid or other material (not shown) may be provided between the lens 466 and the optical imaging bundle 464 to minimize losses and/or reflection at the transition, as is known to those skilled in the art.

Figure 6:
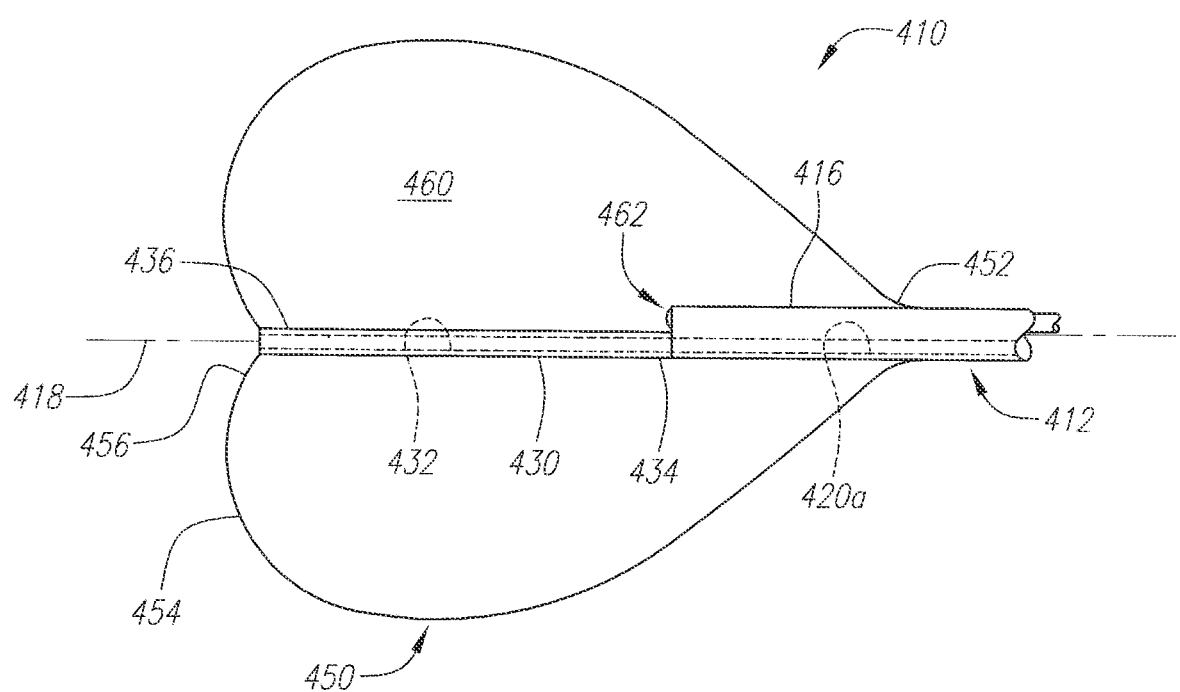
FIG. 6 is a cross-sectional side view of a distal end of another embodiment of an apparatus for cannulating a body lumen, in accordance with the present invention.

Turning to FIG. 10 with continued reference to FIG. 6, a tubular extension 430 may extend from the distal end 416 of the catheter 412. The tubular extension 430 may include a lumen 432 extending between proximal and distal ends 434, 436 of the tubular extension 430. Preferably, the tubular extension 430 has a substantially smaller diameter or other cross-section than the distal end 416 of the catheter 412.

The proximal end 434 of the tubular extension 430 may be attached to the distal end 416 of the catheter 412 such that it is coextensive with the cannulation lumen 420a. Thus, an instrument or fluid introduced through the cannulation lumen 420a may pass freely through the lumen 432 of the tubular extension 430. In addition, attaching the tubular extension 430 eccentrically to the catheter 412 opposite the optical imaging bundle 464 may minimize the extent that the tubular extension 430 obstructs the field of view of the optical imaging bundle 464.

In one embodiment, the proximal end 434 of the tubular extension 430 may be at least partially received in the cannulation lumen 420a or in a recess (not shown) concentric with the cannulation lumen 420a. Alternatively, the proximal end 434 of the tubular extension 430 may be butted against the distal end 416 of the catheter 412. In addition or alternatively, the tubular extension 4430 may be bonded to the catheter 412, e.g., using an adhesive, heating, sonic welding, and the like.

The balloon 450 may include a proximal end 452 attached to the distal end 416 of the catheter 412 and a distal end 456 attached to the distal end of the tubular extension 430. The proximal end 452 of the balloon 450 may be secured to the outer surface of the catheter 412, e.g., using an adhesive, heating, an interference fit, an outer collar (not shown), and the like, similar to the other embodiments described herein.

Turning to FIGS. 12A-12D, an imaging apparatus 10, such as any of those described elsewhere herein, may be included in a system or kit, along with an elongate rail 80, and/or a lead 100. As shown, the elongate rail 80 is a guidewire including a proximal end (not shown), a distal end 83, and one or more fixation elements 82 on the distal end 83. In the exemplary embodiment shown, the fixation element 82 is a helical screw, which may include a sharpened tip to facilitate penetration into tissue. As the guidewire 80 is rotated about its longitudinal axis, the helical screw 82 may be screwed into tissue. To remove the helical screw 82, the guidewire 80 may be rotated in the opposite direction.

In alternative embodiment, the fixation element 82 may include other structures, e.g., that actively secure the distal end 83, e.g., adhesives, hooks, pinchers, barbs, and the like.

If the guidewire 80 is secured within a body lumen, e.g., a pulmonary artery, coronary vein, and the like, the fixation element 82 may be an expandable device, e.g., a balloon or mechanically expandable device that may frictionally or otherwise engage surrounding tissue to secure the distal end 83.

Figure 12A:
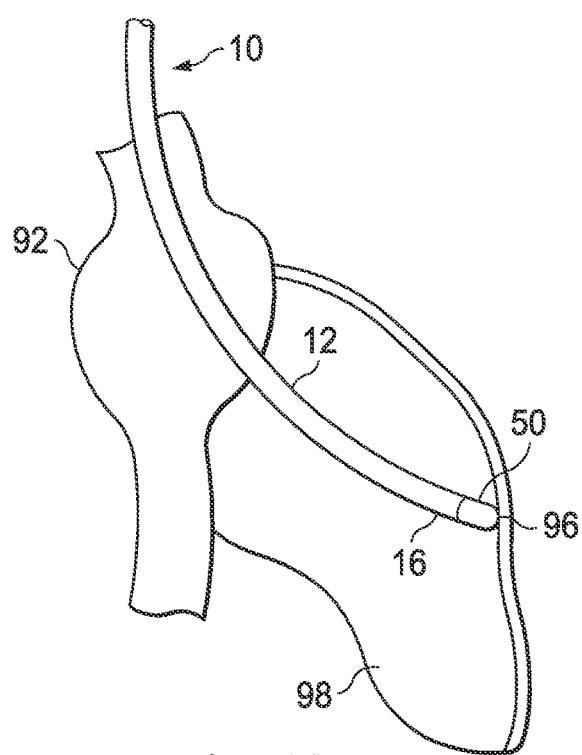
FIGS. 12A-12D are cross-sectional views of a portion of a heart, showing a method for delivering a lead into a right ventricle of the heart.

During use, the imaging apparatus 10 and rail 80 may be used to deliver a pacing or other transvenous lead into a patient's body, e.g., endoluminally to a target location within a body lumen or cavity, or surgically into body cavities, such as the thoracic cavity for epicardial lead placement. FIGS. 12A-12D show an exemplary endocardial placement. Initially, as shown in FIG. 12A, the imaging apparatus 10 may be advanced through the patient's vasculature, from a percutaneous entry site, e.g., at a subelavian or femoral vein, into the patient's heart. As shown, the distal end 16 of the imaging catheter 12 may be introduced through the right atrium 92 and into the right ventricle 98.

An imaging device, e.g., including expandable member 50 and one or more lenses or other imaging assemblies may be used to visualize the interior of the right ventricle 98 to facilitate identifying a suitable delivery location 96. For example, with the expandable member 50 expanded, the distal end 16 may be directed against a wall of the right ventricle 98, e.g., against the right ventricular septum, and manipulated to move the expandable member 50 (and imaging assembly) along the wall to identify a target delivery location 96.

Figure 12B:
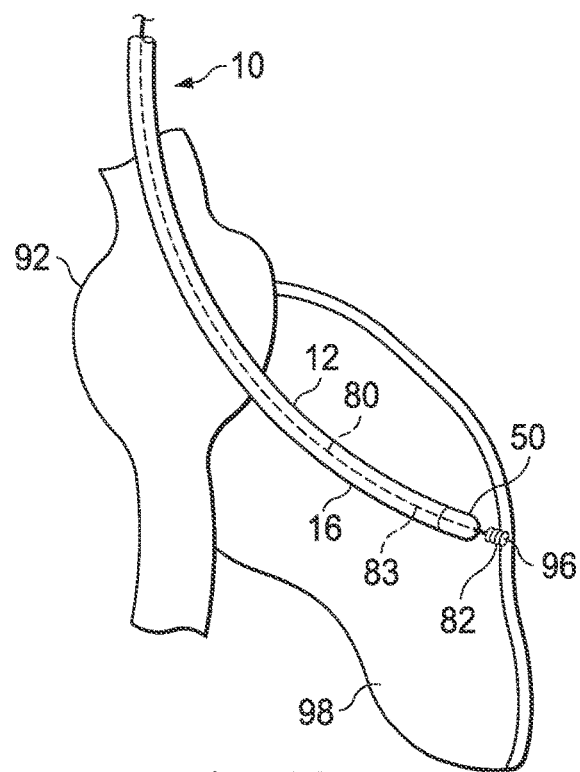

Turning to FIG. 12B, once a target location 96 is identified, the elongate rail 80 is introduced via the imaging apparatus 10 to the target delivery location. As shown, the rail 80 is a guidewire that may be through an instrument lumen (not shown) in the imaging apparatus 10, e.g., from the proximal end (not shown) to the distal end 16 until the guidewire 80 is disposed adjacent or beyond the expandable member 50 at the delivery location 96. The fixation element 82 on a distal end 83 of the guidewire 80 may be used to secure the guidewire 80 to the right ventricle 98 at the target location 96.

In an alternative embodiment, the rail may include a sheath or other tubular member (not shown) that may be advanced through a lumen of the imaging apparatus 10 or may be advanced around the imaging apparatus 10. The tubular member may include one or more fixation elements on the distal end, which may be used to secure the tubular member to the target location 96.

Figure 12C:
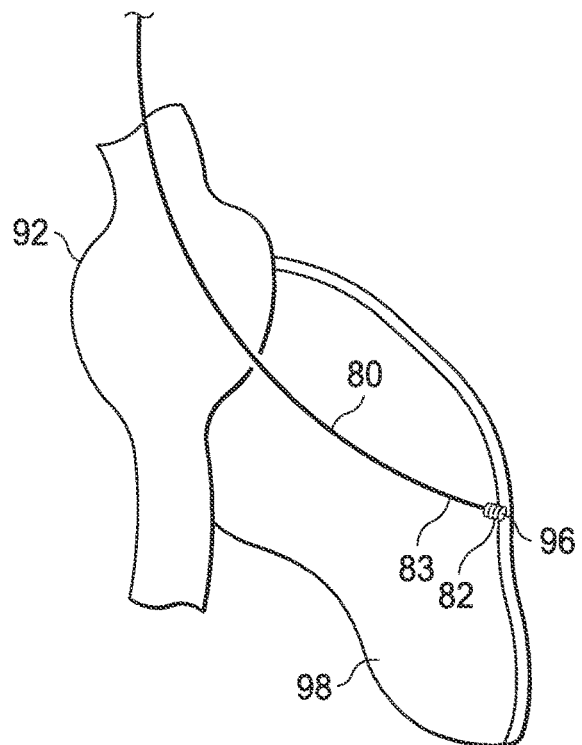

Turning to FIG. 12C, the imaging apparatus 10 may then be removed, leaving the rail 80 secured within the right ventricle 98. For example, the expandable member 50 may be collapsed, and the imaging apparatus 10 removed over (or through) the rail 80.

Figure 12D:
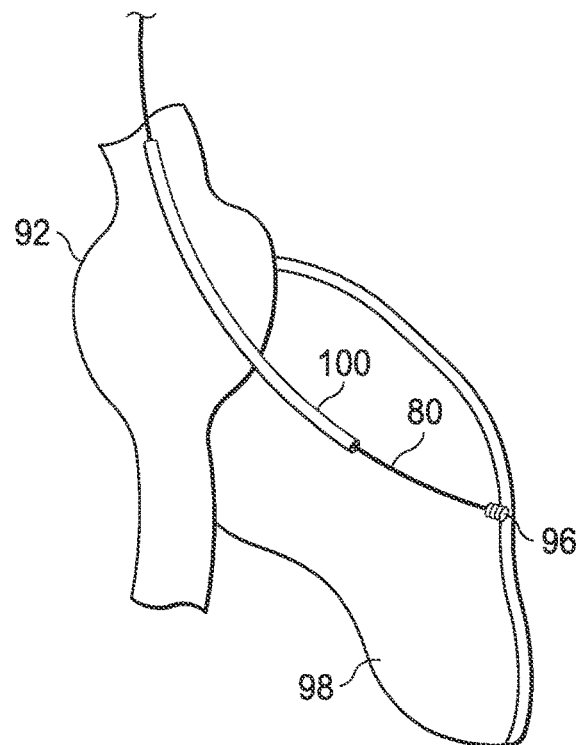

As shown in FIG. 12D, an electrical pacing lead 100 and/or other instrument may then be advanced through the heart via the rail 80 until the lead 100 is disposed within the right ventricle 98 at the delivery location 96. Because cardiac leads are extremely flexible or floppy, the relative strength and/or rigidity of the guidewire 80 may facilitate advancing the lead 100 through larger vessels, where the lead 100 may otherwise wander or bind up. The lead 100 may then be affixed to the delivery location 96, by attaching the fixation element to the delivery location. As shown, the lead 100 include a lumen for receiving the rail 80 therethrough, thereby allowing the lead to be advanced over the rail 80. Alternatively, the lead 100 may be introduced through a lumen of the rail, e.g., if the rail is a sheath or other tubular member (not shown).

The lead 100 may include a helical screw (not shown) or other fixation element, similar to the rail 80 for securing the lead 100 relative to the target location 96. In this embodiment, the rail 80 may be removed, either before or after securing the lead 100 to the target location 96. Alternatively, the rail 80 may remain secured at the target location 96. In this alternative, the lead 100 may include one or more connectors that may secure the lead 100 to the rail 80, thereby securing the lead relative to the target location 96.

In the another embodiment shown in FIG. 13A-13D, an imaging apparatus 10, such as those described elsewhere herein, may be advanced into a body cavity, e.g., into a thoracic cavity. For example, the heart may be exposed using a sternotomy or a minimally invasive approach, e.g., involving one or more ports (not shown) may be used to access the thoracic cavity and/or pericardial sac of the heart.

Figure 13A:
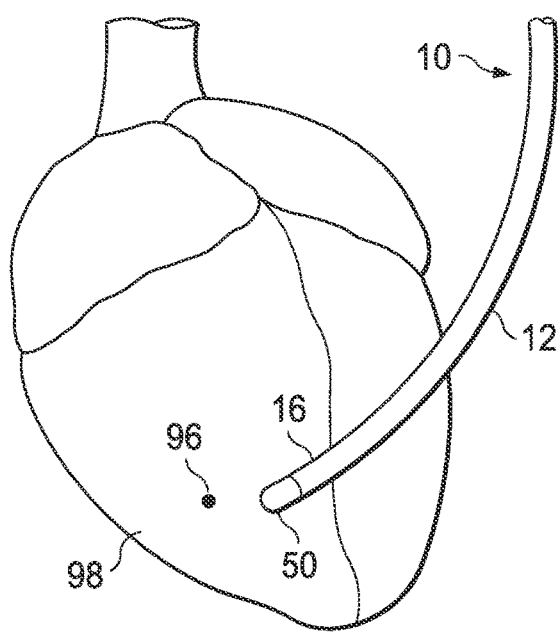
FIGS. 13A-13D are top views of a heart, showing a method for securing an epicardial lead to a heart.

As shown in FIG. 13A, a distal end 16 of the imaging catheter 12 may be disposed adjacent the patient's heart. The imaging apparatus 10 is maneuvered through the pericardial space (not shown) until the expandable member 50 is placed against the epicardium of the heart. The expandable member 50 may be expanded, and the epicardium imaged to identify a target delivery location 96, e.g., above the right ventricle 98. An imaging assembly (not shown) in the expandable member 50 may be used to directly visualize the exterior of the right ventricle 98, which may facilitate identifying a suitable delivery location 96.

Figure 13B:
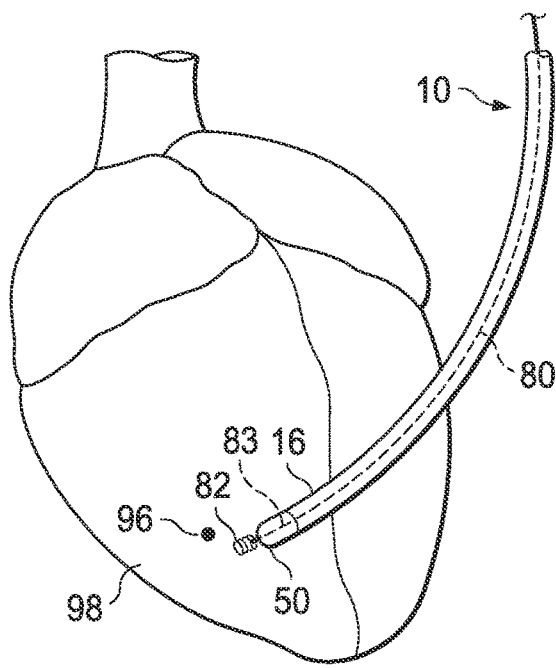

Turning to FIG. 13B, an elongate rail 80 may be advanced through a lumen (not shown) in the imaging apparatus 10, e.g., from a proximal end (not shown) to the distal end 16, until the rail 80 is disposed beyond the expandable member 50 at the delivery location 96. A fixation element 82 on a distal end 83 of the guidewire 80 may be used to secure the guidewire 80 to the epicardium of the heart at the target location 96. As shown, the fixation element 82 is a helical screw, similar to the previous embodiment.

Figure 13C:
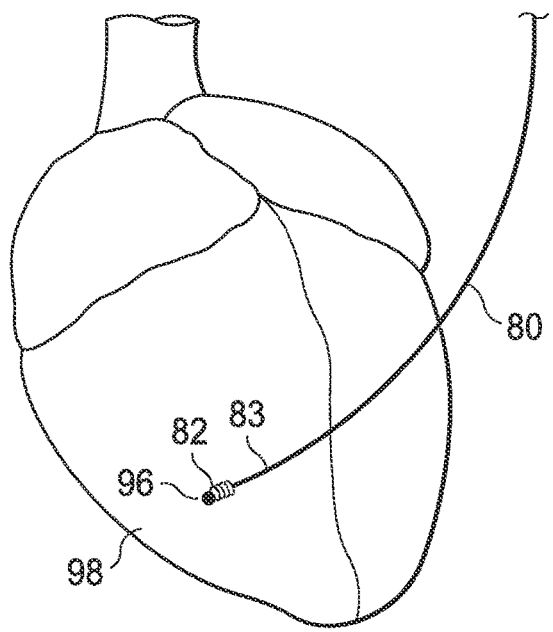
Figure 13D:
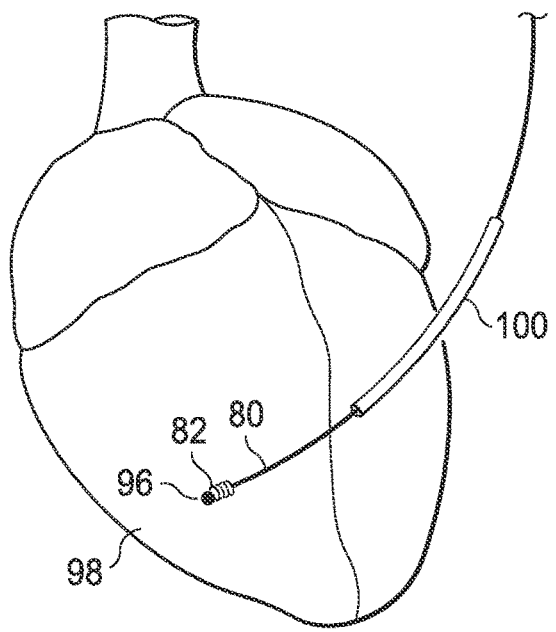

Turning to FIG. 13C, the imaging apparatus 10 may then be removed, leaving the rail 80 secured to the target location 96. As seen in FIG. 13D, an electrical pacing lead 100 and/or other instrument may then be advanced through the pericardial space along the rail 80 until the lead 100 is disposed adjacent the delivery location 96. Because cardiac leads are extremely flexible or floppy, the relative strength and/or rigidity of the rail 80 may facilitate advancing the lead through the pericardial space, where the lead 100 may otherwise wander or bind up. The lead 100 may then be affixed to the delivery location 96, by attaching a fixation element (not shown) on the lead 100 to the delivery location 96. The guidewire 80 may then be removed. Alternatively, the guidewire 80 may remain secured at the delivery location 96.

Alternatively and/or in addition, the apparatus previously described herein may also incorporate deflectability, steerability, and/or a pre-shaped element or a combination of these features in order to achieve further improved navigability.

Although different embodiments have been described herein with particularity as including specific components and/or features, it will be appreciated that each of the embodiments described above may include components and/or features specifically described with respect to individual embodiments. For example, any of the embodiments described above may include one or more of the following: a handle on a proximal end of a catheter, one or more pullwires or other steering elements for steering a catheter and/or a localization/stabilization member, steering controls or actuator, a source of light, a capture device, e.g., including a display, processor for analyzing image data, and/or memory for storing imaging data, sources of fluid e.g., for delivering inflation media, diagnostic, and/or therapeutic agents, and the like. Thus, different components may be provided on each of the embodiments, depending upon a specific application.

In addition, each of the apparatus described may be used to perform any of the procedures described herein and should not limited to the specific examples described. For example, any of the apparatus described may be used for imaging, accessing, and/or cannulating a collapsible lumen, such as the colon. Embodiments with channels through balloons or other expandable and/or displacement members may be used to deliver insufflation media, e.g., carbon dioxide, nitrogen, and/or air, into a collapsible lumen to facilitate performing a procedure therein.

While the invention is susceptible to various modifications, and alternative forms, specific examples thereof have been shown in the drawings and described herein in detail. It should be understood, however, that the invention is not to be limited to the particular forms or methods disclosed, but, to the contrary, the invention is to cover all modifications, equivalents and alternatives falling within the scope of the appended claims.

We claim:

1. A catheter system comprising:
   an elongate catheter body including a distal end and a ridge, the ridge formed as part of the elongate catheter body;
   a cannulation lumen extending through the elongate catheter body and terminating at the distal end of the elongate catheter body;
   a steering element extending through the elongate catheter body for steering the distal end of the elongate catheter body; and
   an imaging element secured to a distal end portion of the elongate catheter body and configured to obtain optical images of an area located distally of the distal end of the elongate catheter body,
   wherein the ridge extends axially along an outer surface of the distal end portion, wherein a width of the ridge measured about a circumference of the elongate catheter body is less than a length of the ridge measured along a longitudinal axis of the elongate catheter body, and wherein the imaging element is radially aligned with the ridge with at least a portion of the imaging element disposed within the ridge.

2. The catheter system of claim 1, wherein the steering element steers the distal end of the elongate catheter body by deflecting the distal end transversely relative to the longitudinal axis of the elongate catheter body extending proximal of the distal end.

3. The catheter system of claim 1, further comprising a tubular member extendable from a distal end of the cannulation lumen.

4. The catheter system of claim 3, further comprising an instrument configured to extend through the cannulation lumen and into the tubular member, distally of the distal end of the elongate catheter body.

5. The catheter system of claim 3, wherein the tubular member has an inner diameter smaller than an inner diameter of the cannulation lumen.

6. The catheter system of claim 1, further comprising an imaging lumen extending at least partially through the elongate catheter body and terminating at the distal end of the elongate catheter body, wherein the imaging element is configured to extend within the imaging lumen.

7. The catheter system of claim 1, wherein the imaging element comprises a lens.

8. The catheter system of claim 7, wherein the imaging element further comprises a fiber optic bundle, wherein the lens is coupled to the fiber optic bundle.

9. The catheter system of claim 1, wherein the imaging element comprises a CMOS sensor.

10. The catheter system of claim 1, wherein the imaging element comprises a CCD sensor.

11. The catheter system of claim 1, further comprising a light source.

12. The catheter system of claim 11, wherein the light source comprises at least one light emitting diode ("LED").

13. The catheter system of claim 11, wherein the light source comprises a first LED and a second LED, wherein the first LED and the second LED are disposed on opposing sides of the imaging element.

14. The catheter system of claim 11, wherein the light source comprises at least one light guide.

15. The catheter system of claim 14, wherein the at least one light guide comprises a first light guide including a first optical fiber and a second light guide including a second optical fiber, wherein the first light guide and the second light guide are disposed on opposing sides of the imaging element.

16. The catheter system of claim 1, further comprising a steering element lumen extending at least partially through the elongate catheter body, wherein the steering element extends within the steering element lumen.

17. The catheter system of claim 1, further comprising a fluid source adapted to deliver a fluid into the elongate catheter body.

18. The catheter system of claim 17, wherein the cannulation lumen is configured to channel the fluid to the distal end of the elongate catheter body.

19. The catheter system of claim 1, wherein the elongate catheter body includes a distal portion and a proximal portion attached together at a joint.

\* \* \* \* \*